United States Patent [19]

Shults et al.

[11] Patent Number: 4,757,022
[45] Date of Patent: Jul. 12, 1988

[54] BIOLOGICAL FLUID MEASURING DEVICE

[75] Inventors: Mark C. Shults, Madison; Christopher C. Capelli, Kenosha; Stuart J. Updike, Madison, all of Wis.

[73] Assignee: Markwell Medical Institute, Inc., Racine, Wis.

[21] Appl. No.: 122,395

[22] Filed: Nov. 19, 1987

Related U.S. Application Data

[60] Continuation of Ser. No. 852,346, Apr. 15, 1986, which is a division of Ser. No. 852,343, Apr. 15, 1986, and a continuation-in-part of Ser. No. 774,330, Sep. 10, 1985.

[51] Int. Cl.$^4$ .............................................. C12M 1/34
[52] U.S. Cl. .................................... 435/291; 204/415
[58] Field of Search ................. 435/291; 422/90, 98; 436/150, 178; 204/412, 415

[56] References Cited

U.S. PATENT DOCUMENTS

| | | | |
|---|---|---|---|
| 3,933,593 | 1/1976 | Sternberg | 435/291 |
| 3,966,580 | 6/1976 | Janata et al. | 204/195 B |
| 3,979,274 | 9/1976 | Newman | 204/415 |
| 4,040,908 | 8/1977 | Clark | 435/291 |
| 4,151,049 | 4/1979 | Janata | 204/1 T |
| 4,172,770 | 10/1979 | Semersky et al. | 435/291 |
| 4,225,410 | 9/1980 | Pace | 204/412 |
| 4,240,889 | 12/1980 | Yoda et al. | 204/195 B |
| 4,290,431 | 9/1981 | Herbert et al. | 128/635 |
| 4,303,076 | 12/1981 | Danek | 128/635 |
| 4,311,151 | 1/1982 | Hagihara | 128/635 |
| 4,388,166 | 6/1983 | Suzuki et al. | 204/403 |
| 4,418,148 | 11/1983 | Oberhardt | 435/179 |
| 4,454,007 | 6/1984 | Pace | 204/1 T |
| 4,534,355 | 8/1985 | Potter | 128/635 |

FOREIGN PATENT DOCUMENTS 1442303  7/1976  United Kingdom.

OTHER PUBLICATIONS

Ko, Wen H., Implantable Sensors for Closed Loop Prosthetic Systems, Ch. 12, 167–175, Futura Publishing Co. (1985).
ASTM E 96, Standard Test Methods for Water Vapor Transmission of Materials, *Annual Book of ASTM Standards*, 04.06, 776–785, (1986).
Muir et al., *J. Biomed. Mater. Res.*, 5, 415–445 (1971).
Shichiri et al., "Wearable Artificial Endocrine Pancreas with Needle-Type Glucose Sensor", *The Lancet*, 1129–1131 (Nov. 1982).

Primary Examiner—Carroll B. Dority, Jr.
Attorney, Agent, or Firm—Olson & Hierl

[57] ABSTRACT

A biological fluid measuring device for determining the presence and the amounts of substances in a biological fluid without the need for dilution of the fluid comprises a main housing including electronic circuit means and at least one elecrode, and a cartridge having a membrane. The cartridge is removably mounted on the housing and the membrane is operably associated with the electrode. The cartridge also includes means for protecting the membrane when the device is not in use.

29 Claims, 3 Drawing Sheets

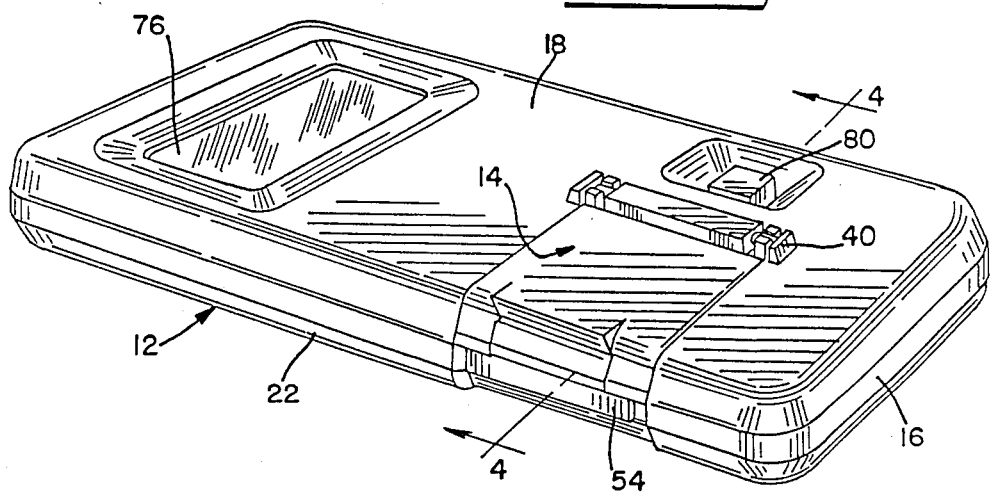
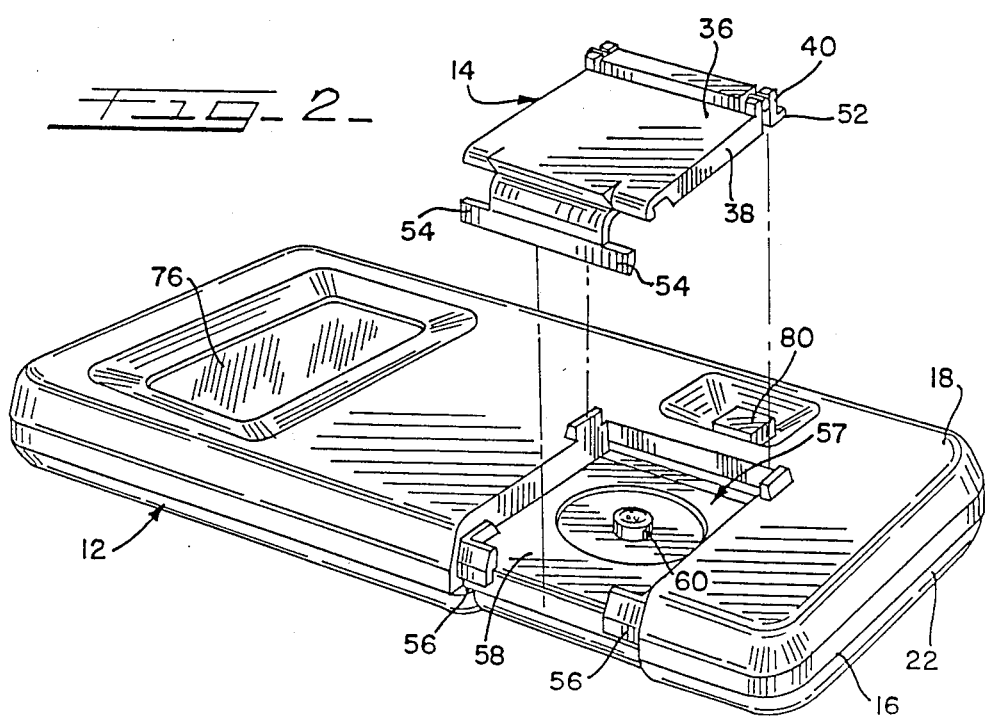

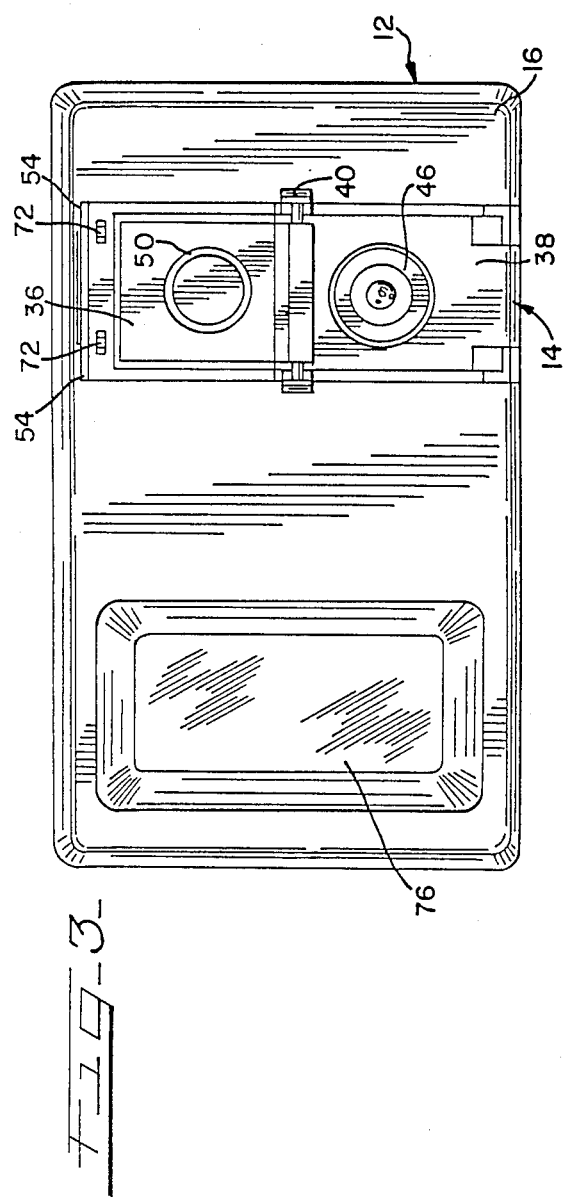
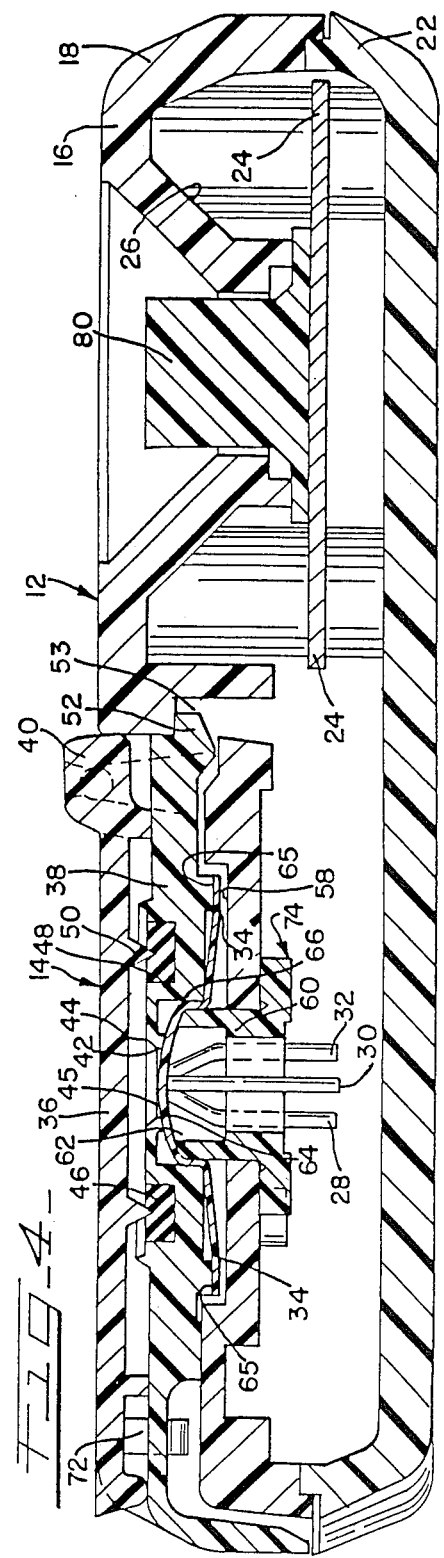

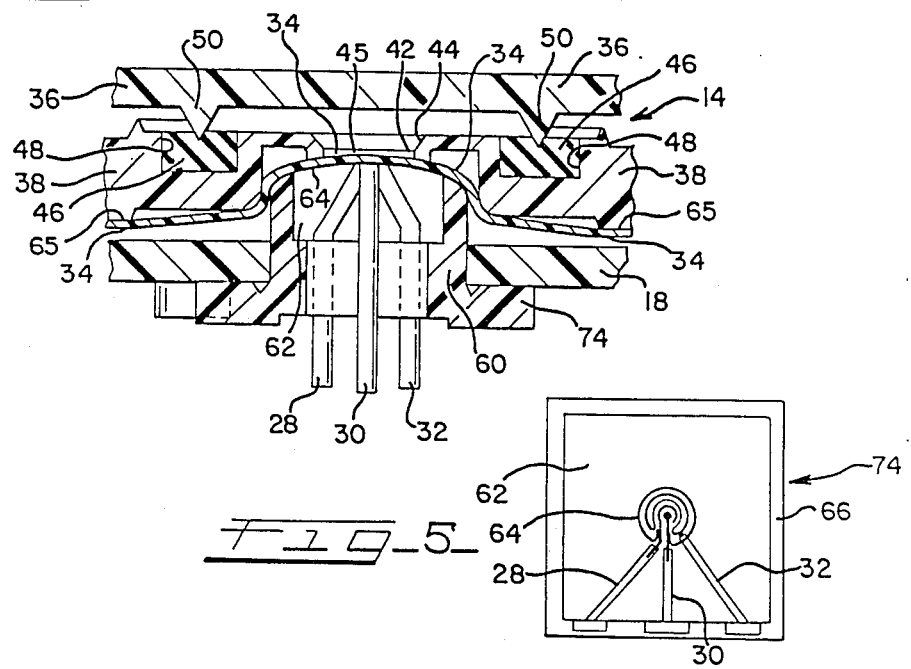
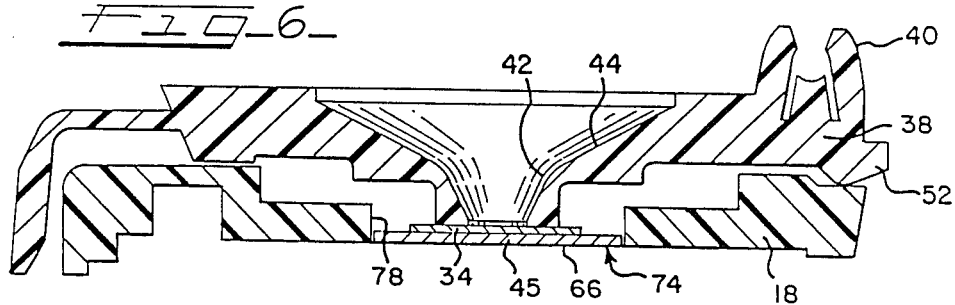
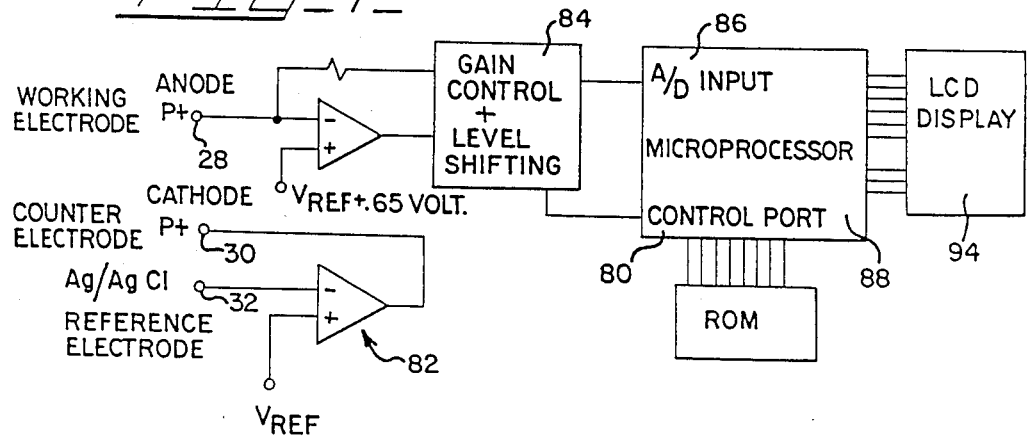

BIOLOGICAL FLUID MEASURING DEVICE

CROSS REFERENCE TO RELATED APPLICATIONS

This application is a continuation of application Ser. No. 852,346, filed Apr. 15, 1986, which was a continuation-in-part of application Ser. No. 774,330, filed Sept. 10, 1985 and a division of application Ser. No. 852,343, filed Apr. 15, 1986.

TECHNICAL FIELD

The present invention relates to devices having replaceable membranes which cooperate with an electrode assembly to determine the amount of a substance in a biological fluid.

BACKGROUND OF THE INVENTION

The continuous measurement of substances in biological fluids is of interest in the study and control of metabolic disorders. Electrode systems have been developed for this purpose whereby an enzyme-catalyzed reaction is monitored by an electrochemical sensor. In such electrode systems, the electrochemical sensor comprises an electrode with potentiometric or amperometric function in close contact with a thin layer containing an enzyme in dissolved or insoluble form. The thin layer may also include a co-enzyme.

In conventional practice, a semipermeable membrane separates the thin layer of the electrode containing the enzyme from the sample of biological fluid that includes the substance to be measured. The electrochemical sensor measures the concentration of the substance involved in the enzyme reaction. For example, the concentration of a co-enzyme or a reaction product can be determined. This concentration may be related to the substrate concentration in the sample by its stoichiometric relationship and by calibration of the electrode system.

A number of enzyme electrodes have been developed, and the operation of those electrodes varies depending on the nature of the enzyme reaction and the particular substance being measured. For example, enzyme electrodes include those that measure: (1) a reactant or product of the enzyme reaction; (2) the consumption of a co-enzyme based on the decrease of its initial concentration and (3) the amount of the reduced or oxidized form of a co-enzyme produced during the enzyme reaction.

The operation of a particular enzyme electrode depends on a number of parameters including diffusion processes, kinetics of the enzyme reaction and the type of electrochemical sensor. In particular, the operation of the electrode can be affected by the diffusion of substances through the semipermeable membrane.

Electrode systems that include enzymes have been used to convert amperometrically inactive substances into reaction products which are amperometrically active. Specifically, in the analysis of blood for glucose content, glucose (which is relatively inactive amperometrically) may be catalytically converted by the enzyme glucose oxidase in the presence of oxygen and water to gluconic acid and hydrogen peroxide. Hydrogen peroxide is anodically active and produces a current which is proportional to the concentration of hydrogen peroxide in the blood sample and thus to the concentration of glucose in the sample.

In a sample of undiluted whole blood, however, a molar excess of plasma glucose is present relative to the amount of plasma oxygen. As a result, if a semipermeable membrane is not included over the enzyme, the concentration of glucose in the sample relative to the concentration of oxygen will be so high that the glucose oxidase-catalyzed reaction of glucose and oxygen to gluconic acid and hydrogen peroxide will be oxygen limited.

The effect of an oxygen limited reaction is that the range of glucose concentrations that can be measured with such an electrode is very limited. In particular, linearity is not achieved above minimal concentrations of glucose. In a clinical setting, linear glucose levels must be obtained at glucose concentrations of at least up to about 500 milligrams per deciliter (mg/dl). Without a semipermeable membrane over the enzyme, linear glucose levels can be obtained only up to about 40 mg/dl. Thus, the purpose of the membrane over the enzyme in a glucose sensing electrode system is to limit the amount of glucose that passes or diffuses through the membrane. This extends the upper limit of linearity of glucose measurement from a low value without the membrane to a high value with the membrane.

The two fundamental diffusion processes by which a semipermeable membrane can limit the amount of a substance that passes therethrough are diffusion through the semipermeable membrane as a monolithic, homogeneous structure and diffusion through the semipermeable membrane as a porous structure. The processes of diffusion of substances through these different types of membranes differ considerably.

A semipermeable membrane can comprise a porous structure consisting of a relatively impermeable matrix that includes a plurality of "microholes" or pores of molecular dimensions. Transfer through these membranes is primarily due to passage of substances through the pores. In other words, the membrane acts as a microporous barrier or sieve.

Examples of materials that may be used to form such membranes include polyethylene, polyvinyl chloride, tetrafluoroethylene, polypropylene, cellophane, polyacrylamide, cellulose acetate, polymethyl methacrylate, silicone polymers, polycarbonate, cuprophane and collagen.

Selectivity in such a membrane can be explained on the basis of the molecular size of the diffusing substances. For substances much smaller than the diameter of the pores, passage of the substance through the membrane is relatively unimpeded. As the effective molecular diameter of the substance approaches the diameter of the pore, the pore will exert a drag on the diffusing substance, reducing its permeability to a value lower than that expected on the basis of the membrane porosity. If the molecules of the substance are too large, they will not pass through the membrane at all.

Since transfer is due primarily to passage of the substance through pores, the permeability is directly related to the size of the pores and to the molecular volume of the diffusing substance. As a result, there is little selectivity in the separation of two chemically or structurally related molecules, except when their molecular size is approximately the same as the size of the pore. When this occurs, there is the possibility that forces acting between the substance and the surface of the pore channel may influence the rate of transfer.

Also, the upper size limit to diffusion will be determined by the largest pore diameter, and the overall diffusion rate will depend on the total number of pores for movement of the substance.

Passage of a substance through a monolithic, homogeneous membrane, on the other hand, depends upon dissolution and diffusion of the substance as a solute through a solid, non-porous film. As used herein, the term "monolithic" means substantially non-porous and having a generally unbroken surface. The term "homogeneous", with reference to a membrane, means having substantially uniform characteristics from one side of the membrane to the other. However, a membrane may have heterogeneous structural domains, for example, created by using block copolymers, and still be characterized functionally as homogeneous with respect to its dependence upon dissolution rather than sieving to effect separation of substances. A monolithic membrane can thus be used to separate components of a solution on the basis of properties other than the size, shape and density of the diffusing substances. The membrane acts as a barrier because of the preferential diffusion therethrough of some substance (a solute).

Despite advances in membrane technology, devices that include semipermeable membranes which have been used to detect and measure the presence of a substance in a biological fluid have generally been restricted to laboratory environments. This is because the devices are generally large and complex and require extensive training to operate. In addition, these devices have been somewhat limited because of the difficulty in replacing a membrane used with the electrode.

A need exists for an improved device that selectively measures the presence and the amounts of particular substances in biological fluids. Such a device should accurately measure the amount of a substance in a sample without dilution or pretreatment of the sample. In addition, a basis for selecting appropriate membrane materials for use in such devices is needed. The device should also be easy to use and provide a means for replacing the membrane as necessary.

SUMMARY OF THE INVENTION

The present invention relates to a biological fluid measuring device which permits rapid and accurate determination and measurement of the amount of a particular substance in a biological fluid such as blood.

Generally, the device includes a main housing carrying electronic circuit means and at least one electrode. In a preferred embodiment, at least two electrodes are carried by the housing. A cartridge is removably mounted on the housing. The cartridge includes a membrane which is operably associated with the electrodes when the cartridge is mounted on the housing. It is, of course, possible to design a device wherein one electrode is carried by the housing and a second electrode is carried by another component of the device, as by the cartridge. For ease of description, however, the present device will be described as including at least two electrodes carried by the housing. The cartridge also includes means for protecting the membrane from the ambient surroundings when the device is not in use.

In a preferred embodiment, the housing includes a case having an upper portion and a lower portion which together define a cavity. The electronic circuit is received within the cavity. The electrode is carried by a post which extends upwardly from a base surface defined by the upper portion of the case.

The cartridge preferably includes a body portion which is releasably mounted on the upper portion of the case and a cover which is movably mounted as by a hinge on the body portion. The body portion preferably defines a sidewall which together with the membrane defines a well. The well receives the biological fluid such as a droplet of blood. Because of the particular design of the present invention, the well can be particularly small thereby minimizing the amount of biological fluid sample needed for analysis. In the case of blood, this minimizes both the emotional and physical trauma to the patient.

The body portion preferably includes a collar which extends about the post such that, when the cartridge is mounted on the case, the membrane is placed in contact with the electrodes and is stretched over the surface of the electrodes. This insures good operative contact between the electrodes and the membrane.

The electrodes, the supporting structure for the electrodes such as the post, and the membrane together form an electrode assembly. The membrane is a multilayered structure including layers formed of materials such as polyethylene, polyvinyl chloride, tetrafluoroethylene, polypropylene, cellophane, polyacrylamide, cellulose acetate, polymethyl methacrylate, silicone polymers, polycarbonate, cuprophane, collagen and block copolymers thereof. The membrane prevents direct contact of the fluid sample with the electrodes, but permits selected substances of the fluid to pass through the membrane for electrochemical reaction with the electrodes.

In a particularly preferred embodiment, the membrane is a semi-permeable multilayered membrane having at least one layer formed of a nonporous block copolymer having hydrophobic segments and hydrophilic segments that limits the amount of a substance passing therethrough and a second layer including an enzyme that reacts with the substance to form a product.

In a more preferred embodiment, the electrode assembly comprises an electrode, a first (outer) layer of a block copolymer that limits the amount of a hydrophilic substance passing therethrough, a second (intermediate) layer of a block copolymer including an enzyme bound to the first layer and a third (inner) layer of a block copolymer bound to the second layer and covering the surface of the electrode. The third layer is permeable to relatively low molecular weight substances, such as hydrogen peroxide, but restricts the passage of higher molecular weight substances.

In a preferred embodiment, the enzyme is glucose oxidase and the substance to be measured is glucose. The amount of glucose, for example, in an aliquot of undiluted whole blood, is determined by measuring the amount of hydrogen peroxide produced during the oxidation of glucose to gluconic acid by the enzyme.

The present invention, however, is not limited to the measurement of glucose concentrations, and other enzyme-substrate systems can be used. Examples of other enzymes include galactose oxidase, uricase, cholesterol oxidase, alcohol oxidase, lactose oxidase, L-amino acid oxidase, D-amino acid oxidase, xanthine oxidase and ascorbic acid oxidase.

Nonetheless, to demonstrate the improvement of this invention over other membrane systems, the invention will be described in terms of measuring glucose concentrations based on the production of hydrogen peroxide by the action of glucose oxidase.

The membrane systems currently available are based on semipermeable membranes with microholes or pores. With these membranes there is little selectivity in the separation of substances that are rather close in size, except when the molecular diameters of the substances approach the diameters of the pores. When this occurs, forces between the substance and the surface of the pore channel may influence the rate of transfer.

The layers of the preferred multilayered membrane described herein each comprise homogeneous, monolithic membranes and differ in composition, structure and operation from conventional microporous membranes. This represents a substantial improvement over current membrane systems in terms of ease of manufacturing, lifetime of enzyme activity, and the ability to measure the concentrations of substances in undiluted samples.

In summary, passage of substances through the membranes described herein depends upon dissolution and diffusion of the substance through a solid, non-porous film. Components of a solution can be separated on the basis of properties other than the size, shape and density of the diffusing substance.

BRIEF DESCRIPTION OF THE DRAWINGS

FIG. 1 is a perspective view of biological fluid measuring device of the present invention showing a cartridge received on a housing;

FIG. 2 is an exploded perspective view of the device of FIG. 1 showing the cartridge above and separated from the housing;

FIG. 3 is a top plan view of the device of FIG. 1 showing the cover of the cartridge open and the membrane exposed;

FIG. 4 is a side elevational view taken in section along the plane 4—4 of FIG. 1;

FIG. 4a is an enlarged view of the portion of FIG. 4 that is outlined in phantom;

FIG. 5 is a top plan view of a second embodiment of the electrode assembly;

FIG. 6 is a side elevational view showing a device including the electrode assembly of FIG. 5 taken in section along a plane similar to that shown as plane 4—4 of FIG. 1; and FIG. 7 is an electronic circuit diagram in block form.

DETAILED DESCRIPTION OF THE INVENTION

The present invention relates to a biological fluid measuring device which permits rapid and accurate measurement of the amount of a particular substance in a biological fluid. One particular use of the present invention is to determine the level of glucose in blood using only a small sample. This is a particularly important measurement for individuals having diabetes, and the device is a substantial development over devices that are now being used by individuals with diabetes to determine glucose levels.

Referring to FIGS. 1 and 2, the measuring device comprises a main housing 12 and a cartridge 14 which is removably mounted on the housing (see FIG. 2). This permits the cartridge 14 which can be made disposable to be easily replaced as needed. The construction of the cartridge will be described in detail with reference to FIGS. 4 and 4a. The housing 12 includes a case 16 having an upper portion 18 and a lower portion 22. The upper portion 18 and lower portion 22 are connected together by any particular fastening means such as several screws which are not shown.

Referring also to FIGS. 3 and 4, the main housing 12 also includes electronic circuit means which can be carried in part on a circuit board 24. The electronic circuit means is preferably maintained in a cavity 26 which is defined by the case 16. The housing also includes at least one electrode. In the embodiment shown in FIG. 4, three electrodes 28, 30 and 32 are shown.

The operation of these electrodes is discussed in more detail below. The cartridge 14 includes a membrane 34 which is operably associated with the electrodes 28, 30, and 32 when the cartridge is removably mounted on the housing 12. The cartridge 14 also includes means for protecting the membrane when not in use. The protection means is preferably a cover 36 which is movably mounted on a body portion 38 of the cartridge 14. Alternatively, the cover 36 may be mounted on the case 16. In the illustrated embodiment, the cover 36 is movably mounted on the body portion 38 by a hinge assembly 40.

Generally, the cover 36 has a first position such as shown in FIGS. 1 and 4 in which it protects the membrane 34 and a second position such as shown in FIG. 3 which permits access to the membrane. Access to the membrane 34 is necessary to place the biological fluid sample on the membrane for analysis.

As is more clearly shown in FIG. 4a (which is an enlarged view of the area outlined in phantom in FIG. 4), the body portion preferably defines an opening having a sidewall 42 which together with a portion of the membrane 34 defines a well 44 having a bottom 45. The bottom 45 of the well is defined at least in part by the membrane 34. The biological fluid sample is placed in the well 44 for analysis.

Generally, the sidewall 42 defines an opening of less than 4 millimeters in diameter and the well 44 has the depth of less than 2 millimeters. As a result, the well has a volume of less than about 0.1 to 0.2 cubic centimeters. This substantially minimizes the size of the biological fluid sample necessary for analysis down to the sample sizes as small as about five microliters. Because the size of the sample can be particularly small, compensation for temperature changes during analysis which was often necessary with previous devices can be avoided.

The protection means of the cartridge 14 preferably also includes means for sealing the well 44 and hence the operative portion of the membrane 34 at the bottom 45 of the well 44 from the ambient surroundings. This can include a flexible gasket 46 which extends about the well 44 and cooperates with the body portion 38 and cover 36. The gasket 46 is preferably mounted in a groove 48 defined by the body portion 38 and is engaged by a ring 50 carried on the cover 36.

When the cover is in its second or closed position such as shown in FIG. 4, the ring 50 engages the gasket 46 to seal the well 44 and membrane 34 from the ambient surroundings and to prevent dehydration of the membrane. This also prevents damage to the membrane by physical intrusion or dirt. The ring 50 is preferably provided with a edged surface which bites into the gasket to provide a particularly effective seal.

A retaining means is also provided for releasably retaining the cartridge 14 and its body portion 38 on the housing 12. The retaining means preferably includes a detent 52 on the cartridge 14 which is received in a recess 53 defined by the upper portion 18 of the case 16. The retaining means also preferably includes at least one, and optimally, two wings 54 on the body portion 38 of the cartridge 14 which are received in one or more slots 56 on the case 16. (See, in particular, FIG. 2). The slots 56 are generally perpendicular to the cover 36 so that opening the cover will not disengage the wings 54 from the slots 56.

The upper portion 18 of the case 16 preferably defines a recessed cell 57 (see FIG. 2) into which the cartridge 14 is received. The bottom portion of the cell 57 is defined by a base surface 58. The electrodes 28, 30 and 32 preferably extend upwardly from the base surface 58. The electrodes are preferably mounted within a post 60 which supports the electrodes as they extend upwardly of the base surface 58. The post is preferably generally annular in design with the interior portion thereof filled with an electrically nonconductive support material 62 such as a hardened polyepoxide-containing resin. The electrically nonconductive support material 62 and the top portions of the electrodes define a membrane contact surface 64. The membrane contact surface 64 is preferably generally dome-shaped such that the membrane 34 can be stretched over the contact surface to more effectively place the membrane in operative association with the electrodes.

The body portion 38 preferably also includes a collar 66 which extends opposite of the well 44 with respect to the membrane 34 where it defines the bottom 45 of the well. As shown in FIG. 4, the collar 66 extends about the post 60. The membrane 34 is preferably attached to a retaining surface 65 by an adhesive at the edge of the collar 66 with the portion of the membrane within the collar being free to move. As the cartridge 14 is mounted on the housing 12, the membrane is then stretched over the post 60 providing continuous contact between membrane 34 and the contact surface 64.

The cover 36 is preferably provided with a closure means 72 such as one or more latches which engage the body portion 38. Generally, the force necessary to disengage the closure means 72 from the body portion 38 should be less than that necessary to disengage the wings 54 from the slots 56. In this manner, the operator can easily open the cover 36 without accidentally disengaging the cartridge 14 from the main housing 12.

The electrodes 28, 30 and 32 together with support assembly such as post 60 and the membrane 34 comprise the electrode assembly. It is this assembly which is contacted with the body fluid sample for analysis. The electrode assembly 74 is operably associated with the electronic circuit means which analyzes the current from the reaction of the components in the body fluid with the electrodes. The electronic circuit means is in turn operably associated with display means such as a liquid crystal display 76 to indicate amount of glucose in the fluid sample.

Referring to FIG. 5, another embodiment of the electrode assembly 74 is shown wherein the three electrodes 28, 30 and 32 are deposited onto a ceramic surface 66. An electrically nonconductive material 62 is applied as a coating over the electrodes to form an insulating barrier. A portion of each electrode, however, is not coated to form a membrane contact surface 64 so that a membrane can be applied over the electrodes in operative contact therewith.

FIG. 6 shows the electrode assembly 74 of FIG. 5 in the device. In particular, the electrode assembly including the membrane 34 is positioned within a recess 78 in the base surface 58 of the recessed cell 57. The cartridge 14 is then positioned within the recessed cell as described above whereby the bottom 45 of the well 44 in the body portion 38 of the cartridge contacts the membrane 34. A cover 36 (as shown in FIG. 4) can be attached to the body portion 38 to protect the membrane when the device is not in use.

The three electrode configuration in combination with the chemical reactions occurring in the multilayered membrane and on the electrode make possible consistent electrode behavior and, in particular, performance of the reference electrode that is stable with time. It is well known in the art that silver/silver chloride electrodes provide a stable reference system for electrochemical sensors.

A silver/silver chloride electrode is typically formed by treating a silver surface with an oxidant and chloride ions (such as by treatment with ferric chloride or a neutral hypochlorite solution), by electrochemical plating of chloride ions onto a silver surface or by the mechanical forming of silver and silver chloride by sintering or similar processes.

When this type of electrode is used in a two electrode configuration with the reference cathodic, chloride ions will be lost from the reference electrode which eventually leads to unstable electrode behavior. According to the present invention, permanent stable reference electrode behavior is achieved when the hydrogen peroxide produced in the membrane oxidizes the silver metal to silver oxide which is then converted to silver chloride by chloride ion. Advantages include ease of manufacturing of the electrode, self-forming and self-maintaining electrode behavior and long-term reference electrode stability.

The relatively low power needs of the present electrode system, as compared to the relatively high power needs of conventional light reflectance-based methods, permit use of a very compact, lightweight device having an extended battery life. CMOS circuitry is used throughout the device and provides a use-dependent battery life of one to two years.

A representative electronic circuit for the device is shown in FIG. 7, but other circuits may also be employed. See, for example, Implantable Sensors for Closed Loop Prosthetic Systems, edited by Wen H. Ko, ch. 12, pages 167–175, Futura Publishing Co., Mount Kisco, N.Y. (1985), the noted relevant pages of which are incorporated herein by reference.

During operation of the device, glucose from the blood sample produces a current flow at the working electrode 28. Equal current is provided by a counter electrode 30 in a reference circuit 82. The current is converted in an analog section 84 by a current to voltage converter to a voltage which is inverted, level-shifted and delivered to an Analog/Digital (A/D) converter 86 in the microprocessor 88. As part of the calibration circuit means, the microprocessor can set the analog gain via its control port 90. The A/D converter is activated at one second intervals. The microprocessor looks at the converter output with any number of pattern recognition algorithms known to those skilled in the art until a glucose peak is identified. A timer is then activated for about 30 seconds at the end of which time the difference between the first and last electrode current values is calculated. This difference is then divided by the value stored in the memory during instrument calibration and is then multiplied by the calibration glucose concentration. The glucose value in milligram percent or millimoles per liter is then displayed on the LCD display screen 94.

During this operation sequence, prompts or messages may be displayed on the LCD screen to guide the user through the calibration and sample measurement procedures. In addition, prompts may be displayed to inform the user about necessary maintenance procedures, such as "Replace Sensor" or "Replace Battery." An on/off button 80 initiates the operation and calibration sequences.

As indicated above, the membrane is a multilayered structure including layers formed of materials such as polyethylene, polyvinyl chloride, tetrafluoroethylene, polypropylene, cellophane, polyacrylamide, cellulose acetate, polymethyl methacrylate, silicone polymers, polycarbonate, cuprophane, collagen and block copolymers thereof.

In a particularly preferred embodiment, the membrane is a semi-permeable multilayered membrane having at least one layer formed of a nonporous block copolymer having hydrophobic segments (such as silicone polymer segments, aromatic and aliphatic polymer segments, polypropylene oxide segments, polytetra-methylene oxide segments and the like) and hydrophilic segments (such as polyoxyethylene segments, polyvinylpyrrolidone segments, polyvinyl alcohol segments and the like) that limits the amount of a substance passing therethrough and a second layer including an enzyme that reacts with the substance to form a product.

The first layer limits the amount of a substance in a fluid that can pass therethrough. The substance can react with the enzyme in the second layer to produce one or more reaction products. A third layer that is permeable to one of the reaction products, but which restricts the passage of other materials may also be used.

The ability of each layer to limit the amount of a molecule that can pass therethrough may be expressed in terms of the moisture-vapor transmission rate (MVTR) and water swelling of the material that forms the layer. As used herein, the MVTR of a material is measured as described in ASTM E 96, the procedure of which is incorporated herein by reference.

The MVTR of the block copolymer of the first layer should be greater than about 4000 grams per square meter per 24 hours, preferably greater than about 5000 grams per square meter per 24 hours. The water swelling of this layer should be greater than about 5 percent.

The MVTR of the block copolymer of the third layer should be from about 500 to about 4000 grams per square meter per 24 hours. The above values relate specifically to layers that are employed to measure the amount of glucose in a biological sample. It will be understood that block copolymers having different MVTR values can be used to measure the amounts of other substances in biological sample and the description of glucose measurement is only illustrative.

EXAMPLE

A membrane formed of a homogeneous, nonporous block copolymer may be prepared as follows. Polymerization is carried out in a 2-liter glass flask with a detachable top containing five inlets. The inlets provide for nitrogen passage, condenser attachment, stirring, thermometer placing, and ingredient addition. A regulated flow of oxygen-free nitrogen passes from a cylinder, through the apparatus, into a water trap, and to the drain. The contents of the reaction flask are stirred by a Teflon blade connected to an electric motor running at 350 rpm. Air is excluded by a mercury seal. Heat is supplied by an electric mantle and temperature recorded by placing a thermometer in the flask contents. A dropping funnel is used for the addition of ingredients during the reaction.

Thirty grams of dimethylaminoethyl methacrylate and 170 grams of acrylonitrile are used. Potassium persulfate is dissolved in 40 milliliters distilled water and portions of the solution are added in sequence with the foregoing monomers as described in Muir et al., *J. Biomed. Mater. Res.*, 5, 415–445 (1971) which is incorporated herein by reference.

The temperature of the mixture in the flask is maintained at 45–50 degrees C. for about 6 hours. The reaction product is an off-white plasticized polymer. The product is washed with water, filtered and dried in a desiccator under vacuum to provide an off-white powder. A typical yield is about 28 grams with a dimethylaminoethyl methacrylate content (as determined from oxygen content analysis) of about 47 percent and an intrinsic viscosity in dimethylformamide at 25 degrees C. of 1.13 dl/g.

The polymer is dissolved in DMF to provide a 10 percent solution by weight. The solution is filtered under vacuum through a Porosity G1 sintered glass funnel and is stored in a desiccator over phosphorus pentoxide for at least 16 hours. The polymer solution is poured on to a glass plate and is spread as a film by passing a doctor blade across the plate. Solvent evaporation is achieved by maintaining a temperature of 45–50 degrees C. for 8 hours in the region of the plate, while solvent vapor is removed by an extractor fan. The membrane is removed from the glass plate by stripping dry or after being soaked with water.

In the enzyme electrode assembly, the membrane layer nearest the anode (the inner layer) comprises a block copolymer, as described above, which is permeable to hydrogen peroxide but which restricts the passage of higher molecular weight substances. This layer has a preferred thickness of less than about 5 microns, more preferably in the range of about 0.1 to about 5 microns and most preferably in the range of about 0.5 to about 3 microns.

The membrane layer nearest the sample (the outer layer) functions as a diffusion barrier to prevent the passage of high molecular weight substances. This layer, also formed of a block copolymer, when used in an electrode assembly to monitor glucose concentrations in a fluid sample, limits the amount of glucose that passes therethrough. This layer has a preferred thickness of less than about 45 microns, more preferably in the range of about 15 to about 40 microns and most preferably in the range of about 20 to about 35 microns.

The second (intermediate) layer that binds the inner and outer layers together includes glucose oxidase, galactose oxidase, uricase or the like combined with a block copolymer of this invention.

In certain applications, for ease of application in the electrode assembly, an appropriate carrier or frame made of cardboard, rubber or plastic can be secured to the surface of the laminate or multilayered membrane. The frame includes an opening, for example, in the central portion thereof whereby the outer layer of the membrane may be exposed to the electrode.

The electrode assembly of this invention may also be used in the manner commonly employed in the making of amperometric measurements. A sample of the fluid being analyzed is placed in contact with a reference electrode, e.g., silver/silver-chloride, and the electrode of this invention which is preferably formed of platinum. The electrodes are connected to a galvanometer or polarographic instrument and the current is read or recorded upon application of the desired voltage between the electrodes.

The ability of the present device assembly to accurately measure the concentration of substances such as glucose over a broad range of concentrations in fluids including undiluted whole blood samples enables the rapid and accurate determination of the concentration of those substances. That information can be employed in the study and control of metabolic disorders including diabetes.

The foregoing is intended as illustrative of the present invention but is not limiting. It should be understood that numerous variations and modifications can be made without departing from the spirit and scope of the novel concepts of the invention.

What is claimed is:

1. A biological fluid measuring device comprising:
   (a) a main housing including electronic circuit means and at least two electrodes; and
   (b) a cartridge having a membrane and being removably mounted on the housing with the membrane operably associated with the electrodes, the cartridge including means for protecting the membrane when not in use.

2. The biological fluid measuring device of claim 1 wherein the cartridge includes a body portion retaining the membrane and the protection means includes a cover movably mounted on the body portion.

3. The biological fluid measuring device of claim 2 wherein the cartridge includes a hinge for mounting the cover on the body portion.

4. The biological fluid measuring device of claim 2 wherein the body portion and membrane define a well having sides and a bottom with the bottom being defined at least in part by the membrane.

5. The biological fluid measuring device of claim 4 wherein the well has a volume of less than about 0.2 cubic centimeters and is adapted to accept a sample as small as about 5 microliters.

6. The biological fluid measuring device of claim 1 wherein the protection means seals the membrane from ambient air.

7. The biological fluid measuring device of claim 6 wherein the protection means includes a flexible gasket.

8. The biological fluid measuring device of claim 1 further including retaining means for releasably retaining the cartridge on the housing.

9. The biological fluid measuring device of claim 8 wherein the retaining means includes a detent on the cartridge that is received in a recess defined by the housing.

10. The biological fluid measuring device of claim 1 wherein the housing defines a base surface with the electrodes projecting upwardly from the base surface.

11. The biological fluid measuring device of claim 10 wherein the membrane is stretched over and in contact with the electrodes.

12. The biological fluid measuring device of claim 1 wherein the membrane includes a first layer of a nonporous block copolymer having hydrophobic segments and hydrophilic segments that limits the amount of the substance passing therethrough, a second layer of a nonporous block copolymer including an enzyme bound to the first layer, said enzyme reacting with the substance to form a product, and a third layer of a nonporous block copolymer having hydrophobic and hydrophilic segments that is bound to the second layer and covering the surfaces of the electrodes that restricts the passage of the substance therethrough but permits the passage of the product whereby the amount of product formed corresponds to the amount of the substance in the sample.

13. A biological fluid measuring device comprising:
   (a) a case having an upper portion and a lower portion together defining a cavity, the upper portion also defining a recessed cell having a base surface;
   (b) at least two electrodes mounted on the upper portion of the case and extending upwardly from the base surface;
   (c) electronic circuit means carried by the case within the cavity and operably associated with the electrodes for processing a signal from the electrodes;
   (d) display means carried by the case and operably associated with the electronic circuit means for displaying a result; and
   (e) a cartridge having a body portion defining a receiving surface, the cartridge also including a membrane mounted on the receiving surface and a cover movably mounted on the body portion, the body portion being removably mounted in the recessed cell of the upper portion of the case with the membrane operably associated with the electrodes.

14. The biological fluid measuring device of claim 13 wherein the cartridge includes a hinge which movably mounts the cover on the body portion.

15. The biological fluid measuring device of claim 13 wherein the body portion and membrane define a well that is adapted to receive the biological fluid.

16. The biological fluid measuring device of claim 13 including an electrically nonconductive support material about the electrodes, the electrodes and electrically nonconductive support material defining a membrane contact surface.

17. The biological fluid measuring device of claim 16 wherein the membrane is stretched over the membrane contact surface.

18. The biological fluid measuring device of claim 13 including a gasket about the well cooperating with the body portion and cover to seal the well from ambient air.

19. The biological fluid measuring device of claim 13 wherein the electrodes are carried by a post mounted on the upper portion of the case and extending upwardly from the base surface.

20. The biological fluid measuring device of claim 19 wherein the body portion includes a collar which extends about the post, the membrane being attached to the collar.

21. The biological fluid measuring device of claim 19 wherein the post includes an electrically nonconductive support material about the electrodes to retain the electrodes in a fixed position.

22. A biological fluid measuring device comprising:
   (a) a case defining a cavity;
   (b) at least two electrodes mounted on the case;
   (c) electronic circuit means carried in the cavity and operably associated with the electrodes for processing a signal from the electrodes;
   (d) display means carried by the case and operably associated with the electronic circuit means;
   (e) a body portion defining an opening being removably mounted on the case;
   (f) a membrane mounted on the body portion and being operably associated with the electrodes, the membrane and opening together defining a well; and (g) a cover movably mounted on one of the case and body portion, the cover having a first position which permits access to the well and a second position which protects the well from the ambient surroundings.

23. The biological fluid measuring device of claim 22 including a gasket carried by one of the cover and body portion for sealing with the cover and body portion to protect the well when the cover is in its second position.

24. A cartridge for use as part of a biological fluid measuring device having a housing carrying electronic circuit means and at least two electrodes, the cartridge comprising:

(a) a body portion having a side wall defining an opening;

(b) a membrane mounted on the body portion across the opening, whereby the sidewall and membrane together define a well;

(c) means for mounting the body portion on the housing with the membrane operably associated with the electrodes; and (d) a cover movably mounted on the body portion and having a first position which permits access to the well and the second position which protects the well from the ambient surroundings.

25. The cartridge of claim 24 further including a hinge for movably mounting the cover on the body portion.

26. The cartridge of claim 24 further including a gasket and cooperating with the cover and body portion to seal the well from the ambient surroundings when the cover is in its second position.

27. The cartridge of claim 26 wherein the gasket is carried by the body portion and extends about the well, and the cover includes a ring which engages the gasket when the cover is in its second position.

28. The cartridge of claim 24 wherein the body portion includes a collar opposite the well with respect to the portion of the membrane which defines the well, the membrane being attached to the collar.

29. The cartridge of claim 24 wherein the body portion includes at least one wing which engages a slot defined by the housing.

* * * * *